(12) United States Patent
Caselnova

(10) Patent No.: US 9,101,507 B2
(45) Date of Patent: Aug. 11, 2015

(54) APPARATUS AND METHOD FOR PROXIMAL-TO-DISTAL ENDOLUMINAL STENT DEPLOYMENT

(76) Inventor: Ralph F. Caselnova, Amityville, NY (US)

( * ) Notice: Subject to any disclaimer, the term of this patent is extended or adjusted under 35 U.S.C. 154(b) by 162 days.

(21) Appl. No.: 13/474,851

(22) Filed: May 18, 2012

(65) Prior Publication Data

US 2012/0296407 A1    Nov. 22, 2012

Related U.S. Application Data

(60) Provisional application No. 61/519,238, filed on May 18, 2011.

(51) Int. Cl.
*A61F 2/84* (2006.01)
*A61F 2/962* (2013.01)

(52) U.S. Cl.
CPC .................................... *A61F 2/962* (2013.01)

(58) Field of Classification Search
CPC ........... A61F 2/962; A61F 2/95; A61F 2/966; A61F 2002/9505
USPC ................................ 623/1.11; 606/108, 198
See application file for complete search history.

(56) References Cited

U.S. PATENT DOCUMENTS

| | | |
|---|---|---|
| 3,868,956 A | 3/1975 | Alfidi |
| 4,323,071 A | 4/1982 | Simpson |
| 4,468,224 A | 8/1984 | Enzmann |
| 4,512,338 A | 4/1985 | Balko |
| 4,516,972 A | 5/1985 | Samson |
| 4,538,622 A | 9/1985 | Samson |
| 4,553,545 A | 11/1985 | Maass |
| 4,554,929 A | 11/1985 | Samson |
| 4,562,596 A | 1/1986 | Kornberg |
| 4,569,347 A | 2/1986 | Frisbie |
| 4,571,240 A | 2/1986 | Samson |
| 4,572,186 A | 2/1986 | Gould |
| 4,580,568 A | 4/1986 | Gianturco |
| 4,588,403 A | 5/1986 | Weiss et al. |
| 4,616,652 A | 10/1986 | Simpson |
| 4,655,771 A | 4/1987 | Wallsten |
| 4,665,918 A | 5/1987 | Garza |
| 4,723,549 A | 2/1988 | Wholey |
| 4,733,665 A | 3/1988 | Palmaz |
| 4,739,762 A | 4/1988 | Palmaz |
| 4,748,982 A | 6/1988 | Horzewski |
| 4,748,986 A | 6/1988 | Morrison |
| 4,762,128 A | 8/1988 | Rosenbluth |

(Continued)

*Primary Examiner* — Thomas McEvoy
*Assistant Examiner* — Julie A Szpira
(74) *Attorney, Agent, or Firm* — Thomas A. O'Rourke; Bodner & O'Rourke, LLP

(57) ABSTRACT

A prosthetic delivery device is adapted for introducing a stent within a patient's vasculature through a reverse deployment procedure, beginning at a proximal location and finishing at a distal location. The device comprises: a guide tube, a rotation tube, and an outer tube. The guide tube threadably receives the rotation tube thereon. The rotation tube comprises a sheath rotatably secured at one end to overhang over a portion of the outer tube, which is received over a portion of the rotation tube, and which is fixedly secured to the guide tube. Rotating the rotation tube causes its translation relative to the outer tube. A stent crimped to be disposed beneath the sheath is forced to deploy proximally by relative movement of an annular deployment ring on the outer tube. A key on the outer tube is received within a key way of the sheath to prevent its rotation.

15 Claims, 3 Drawing Sheets

(56) References Cited

U.S. PATENT DOCUMENTS

| | | |
|---|---|---|
| 4,787,884 A | 11/1988 | Goldberg |
| 4,790,315 A | 12/1988 | Mueller |
| 4,848,342 A | 7/1989 | Kaltenbach |
| 4,856,516 A | 8/1989 | Hillstead |
| 4,913,141 A | 4/1990 | Hillstead |
| 4,921,484 A | 5/1990 | Hillstead |
| 4,950,227 A | 8/1990 | Savin |
| 4,955,749 A | 9/1990 | Panovic |
| 4,969,458 A | 11/1990 | Wiktor |
| 4,969,890 A | 11/1990 | Sugita |
| 4,990,155 A | 2/1991 | Wilkoff |
| 4,998,539 A | 3/1991 | Delsanti |
| 5,002,560 A | 3/1991 | Machold |
| 5,019,085 A | 5/1991 | Hillstead |
| 5,019,090 A | 5/1991 | Pinchuk |
| 5,026,377 A | 6/1991 | Burton |
| 5,034,001 A | 7/1991 | Garrison |
| 5,035,706 A | 7/1991 | Giantureo |
| 5,037,392 A | 8/1991 | Hillstead |
| 5,037,427 A | 8/1991 | Harada |
| 5,041,126 A | 8/1991 | Gianturco |
| 5,059,166 A | 10/1991 | Fischell |
| 5,059,211 A | 10/1991 | Stack |
| 5,067,957 A | 11/1991 | Jervis |
| 5,071,407 A | 12/1991 | Termin |
| 5,078,720 A * | 1/1992 | Burton et al. ............ 606/108 |
| 5,078,726 A | 1/1992 | Kreamer |
| 5,078,736 A | 1/1992 | Behl |
| 5,089,005 A | 2/1992 | Harada |
| 5,089,006 A | 2/1992 | Stiles |
| 5,092,877 A | 3/1992 | Pinchuk |
| 5,102,417 A | 4/1992 | Palmaz |
| 5,108,416 A | 4/1992 | Ryan |
| 5,116,318 A | 5/1992 | Hillstead |
| 5,122,154 A | 6/1992 | Rhodes |
| 5,123,917 A | 6/1992 | Lee |
| 5,135,517 A | 8/1992 | McCoy |
| 5,137,513 A | 8/1992 | McInnes |
| 5,158,548 A | 10/1992 | Lau |
| 5,163,952 A | 11/1992 | Froix |
| 5,163,958 A | 11/1992 | Pinchuk |
| 5,171,262 A | 12/1992 | MacGregor |
| 5,183,085 A | 2/1993 | Timmermans |
| 5,192,297 A | 3/1993 | Hull |
| 5,201,757 A * | 4/1993 | Heyn et al. ............ 606/198 |
| 5,222,969 A | 6/1993 | Gillis |
| 5,222,971 A | 6/1993 | Willard |
| 5,226,913 A | 7/1993 | Pinchuk |
| 5,242,399 A | 9/1993 | Lau |
| 5,242,451 A | 9/1993 | Harada |
| 5,256,146 A | 10/1993 | Ensminger |
| 5,258,020 A | 11/1993 | Froix |
| 5,263,964 A | 11/1993 | Purdy |
| 5,282,823 A | 2/1994 | Schwarz |
| 5,282,824 A | 2/1994 | Gianturco |
| 5,292,331 A | 3/1994 | Boneau |
| 5,300,085 A | 4/1994 | Yock |
| 5,304,200 A | 4/1994 | Spaulding |
| 5,306,294 A | 4/1994 | Winston |
| 5,316,351 A | 5/1994 | Czimny et al. |
| 5,330,500 A | 7/1994 | Song |
| 5,354,308 A | 10/1994 | Simon |
| 5,354,309 A | 10/1994 | Schnepp-Pesch |
| 5,372,532 A | 12/1994 | Robertson, Jr. |
| 5,372,600 A | 12/1994 | Beyar |
| 5,378,239 A | 1/1995 | Termin |
| 5,380,304 A | 1/1995 | Parker |
| 5,391,172 A | 2/1995 | Williams |
| 5,395,390 A | 3/1995 | Simon |
| 5,403,341 A | 4/1995 | Solar |
| 5,405,377 A | 4/1995 | Cragg |
| 5,411,507 A | 5/1995 | Heckele |
| 5,415,664 A | 5/1995 | Pinchuk |
| 5,421,955 A | 6/1995 | Lau |
| 5,443,496 A | 8/1995 | Schwartz |
| 5,445,646 A | 8/1995 | Euteneuer |
| 5,447,503 A | 9/1995 | Miller |
| 5,449,373 A | 9/1995 | Pinchasik |
| 5,453,090 A | 9/1995 | Martinez |
| 5,456,694 A | 10/1995 | Marin |
| 5,458,615 A | 10/1995 | Klemm |
| 5,464,449 A | 11/1995 | Ryan |
| 5,478,349 A | 12/1995 | Nicholas |
| 5,484,444 A | 1/1996 | Braunschweiler |
| 5,496,277 A | 3/1996 | Termin |
| 5,496,346 A | 3/1996 | Horzewski |
| 5,507,768 A | 4/1996 | Lau |
| 5,514,154 A | 5/1996 | Lau |
| 5,522,883 A | 6/1996 | Slater |
| 5,534,007 A | 7/1996 | St. Germain |
| 5,554,181 A | 9/1996 | Das |
| 5,569,295 A | 10/1996 | Lam |
| 5,571,135 A | 11/1996 | Fraser |
| 5,571,168 A | 11/1996 | Toro |
| 5,603,721 A | 2/1997 | Lau |
| 5,626,600 A | 5/1997 | Horzewski |
| 5,626,603 A * | 5/1997 | Venturelli et al. ............ 623/1.11 |
| 5,634,928 A | 6/1997 | Fischell |
| 5,645,559 A | 7/1997 | Hachtman |
| 5,653,727 A | 8/1997 | Wiktor |
| 5,662,703 A | 9/1997 | Yurek |
| 5,667,522 A | 9/1997 | Flomenblit |
| 5,683,451 A | 11/1997 | Lenker |
| 5,690,644 A | 11/1997 | Yurek |
| 5,693,086 A | 12/1997 | Goicoechea |
| 5,702,418 A | 12/1997 | Ravenscroft |
| 5,707,376 A | 1/1998 | Kavteladze |
| 5,733,267 A | 3/1998 | Del Toro |
| 5,755,777 A | 5/1998 | Chuter |
| 5,759,186 A | 6/1998 | Bachmann |
| 5,759,192 A | 6/1998 | Saunders |
| 5,772,669 A | 6/1998 | Vrba |
| 5,776,142 A | 7/1998 | Gunderson |
| 5,788,707 A | 8/1998 | Del Toro |
| 5,800,517 A | 9/1998 | Anderson |
| 5,817,101 A | 10/1998 | Fiedler |
| 5,817,102 A | 10/1998 | Johnson |
| 5,824,041 A | 10/1998 | Lenker |
| 5,827,321 A | 10/1998 | Roubin |
| 5,836,951 A * | 11/1998 | Rosenbluth et al. .......... 606/108 |
| 5,836,965 A | 11/1998 | Jendersee |
| 5,843,117 A | 12/1998 | Alt |
| 5,876,448 A | 3/1999 | Thompson |
| 5,888,201 A | 3/1999 | Stinson |
| 5,902,317 A | 5/1999 | Kleshinski |
| 5,906,619 A | 5/1999 | Olson |
| 5,910,145 A | 6/1999 | Fischell |
| 5,925,061 A | 7/1999 | Ogi |
| 5,944,726 A | 8/1999 | Blaeser |
| 5,954,764 A | 9/1999 | Parodi |
| 5,968,052 A | 10/1999 | Sullivan |
| 5,968,069 A | 10/1999 | Dusbabek |
| 5,980,533 A | 11/1999 | Holman |
| 5,984,964 A | 11/1999 | Roberts |
| 5,989,280 A | 11/1999 | Euteneuer |
| 6,001,123 A | 12/1999 | Lau |
| 6,004,328 A | 12/1999 | Solar |
| 6,019,778 A | 2/2000 | Wilson |
| 6,024,763 A | 2/2000 | Lenker |
| 6,051,021 A | 4/2000 | Frid |
| 6,056,759 A | 5/2000 | Fiedler |
| 6,059,810 A | 5/2000 | Brown |
| 6,086,610 A | 7/2000 | Duerig |
| 6,093,194 A | 7/2000 | Mikus |
| 6,113,608 A | 9/2000 | Monroe |
| 6,120,522 A | 9/2000 | Vrba |
| 6,123,723 A | 9/2000 | Konya |
| 6,159,228 A | 12/2000 | Frid |
| 6,168,617 B1 | 1/2001 | Blaeser |
| 6,176,843 B1 | 1/2001 | DiCaprio |
| 6,190,360 B1 | 2/2001 | Iancea |
| 6,203,550 B1 | 3/2001 | Olson |
| 6,206,888 B1 | 3/2001 | Bicek |
| 6,228,110 B1 * | 5/2001 | Munsinger ............ 623/1.12 |

(56) References Cited

U.S. PATENT DOCUMENTS

| | | |
|---|---|---|
| 6,248,122 B1 | 6/2001 | Klumb |
| 6,254,611 B1 | 7/2001 | Vrba |
| 6,280,465 B1 | 8/2001 | Cryer |
| 6,287,315 B1 | 9/2001 | Wijeratne |
| 6,344,044 B1 | 2/2002 | Fulkerson |
| 6,350,278 B1 | 2/2002 | Lenker |
| 6,368,344 B1 | 4/2002 | Fitz |
| 6,375,676 B1 | 4/2002 | Cox |
| 6,402,760 B1 | 6/2002 | Fedida |
| 6,425,898 B1 | 7/2002 | Wilson |
| 6,447,522 B2 | 9/2002 | Gambale |
| 6,514,261 B1 | 2/2003 | Randall |
| 6,527,779 B1 | 3/2003 | Rourke |
| 6,530,947 B1 | 3/2003 | Euteneuer |
| 6,565,595 B1 | 5/2003 | DiCaprio |
| 6,572,643 B1 | 6/2003 | Gharibadeh |
| 6,579,297 B2 | 6/2003 | Bicek |
| 6,605,109 B2 | 8/2003 | Fiedler |
| 6,610,068 B1 | 8/2003 | Yang |
| 6,613,014 B1 | 9/2003 | Chi |
| 6,626,934 B2 | 9/2003 | Blaeser |
| 6,652,480 B1 | 11/2003 | Imran |
| 6,666,883 B1 | 12/2003 | Seguin |
| 6,669,716 B1 | 12/2003 | Gilson |
| 6,676,694 B1 | 1/2004 | Weiss |
| 6,849,084 B2 * | 2/2005 | Rabkin et al. ............... 623/1.12 |
| 6,858,034 B1 | 2/2005 | Hijlkema |
| 6,911,039 B2 | 6/2005 | Shiu |
| 7,044,964 B2 | 5/2006 | Jang |
| 7,105,016 B2 | 9/2006 | Shiu |
| 7,122,050 B2 | 10/2006 | Randall |
| 7,419,501 B2 | 9/2008 | Chie |
| 7,833,259 B2 | 11/2010 | Boatman |
| 7,867,268 B2 * | 1/2011 | Shelso ....................... 623/1.11 |
| RE42,525 E * | 7/2011 | Simonson .................... 604/117 |
| 7,992,273 B2 | 8/2011 | Austin |
| 8,696,728 B2 | 4/2014 | Hebert |
| 2004/0127912 A1 * | 7/2004 | Rabkin et al. ............... 606/108 |
| 2007/0088368 A1 * | 4/2007 | Acosta et al. ............... 606/108 |
| 2007/0233222 A1 * | 10/2007 | Roeder et al. .............. 623/1.11 |
| 2007/0255390 A1 * | 11/2007 | Ducke et al. ............... 623/1.11 |
| 2011/0112546 A1 * | 5/2011 | Juan et al. .................. 606/108 |

* cited by examiner

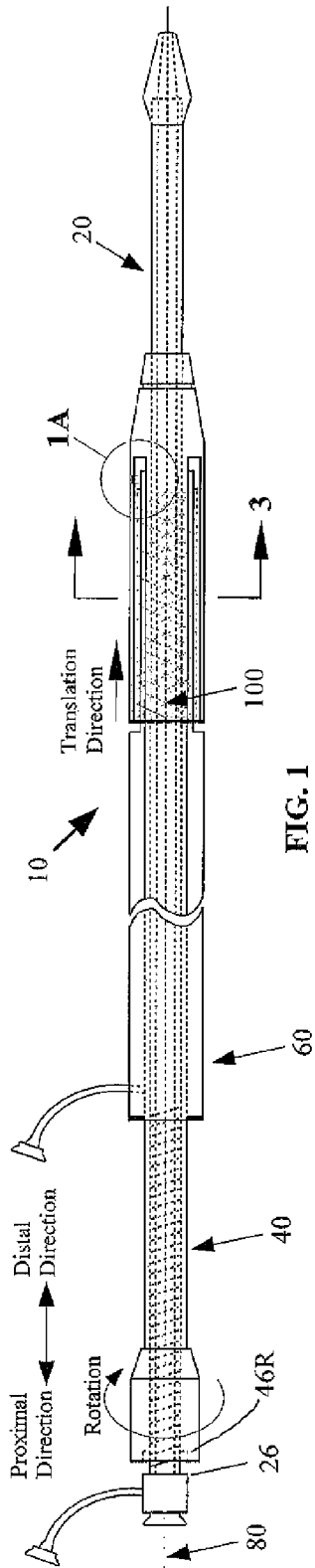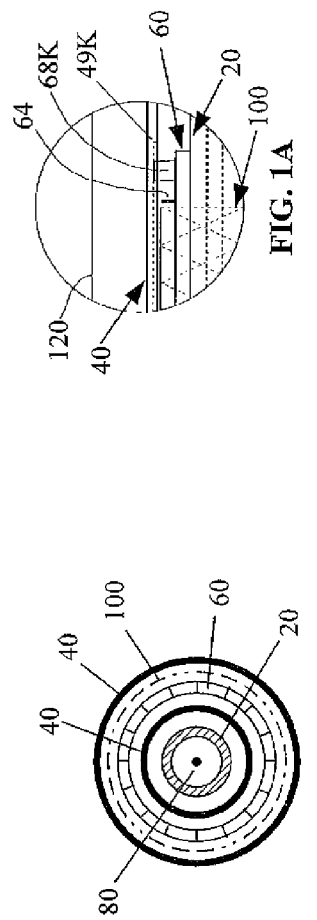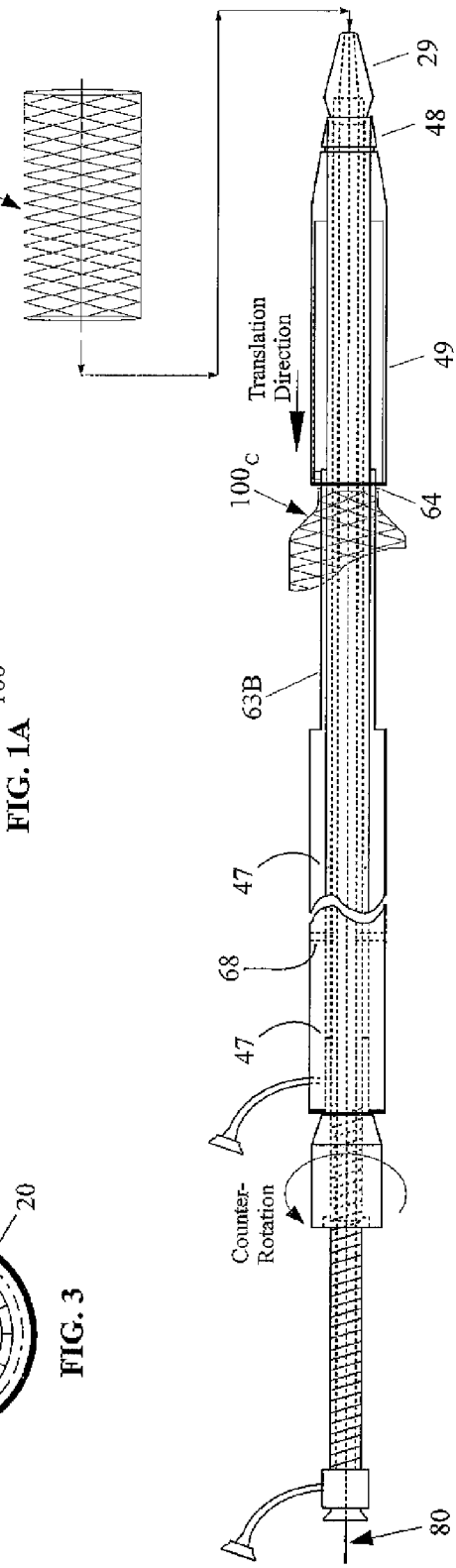

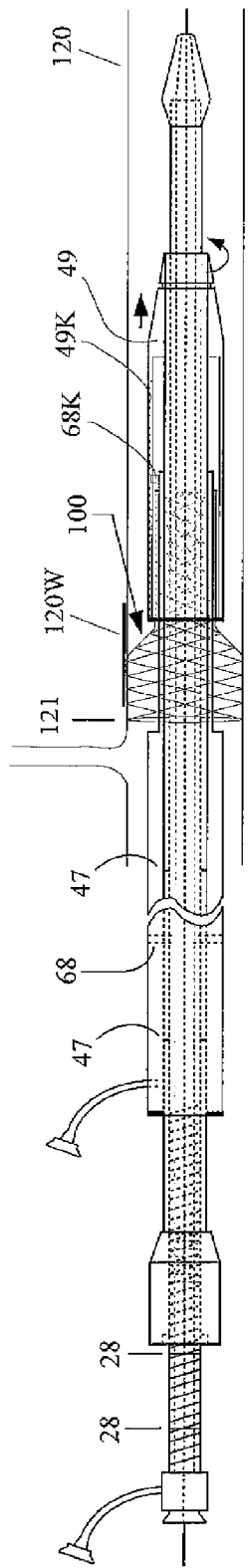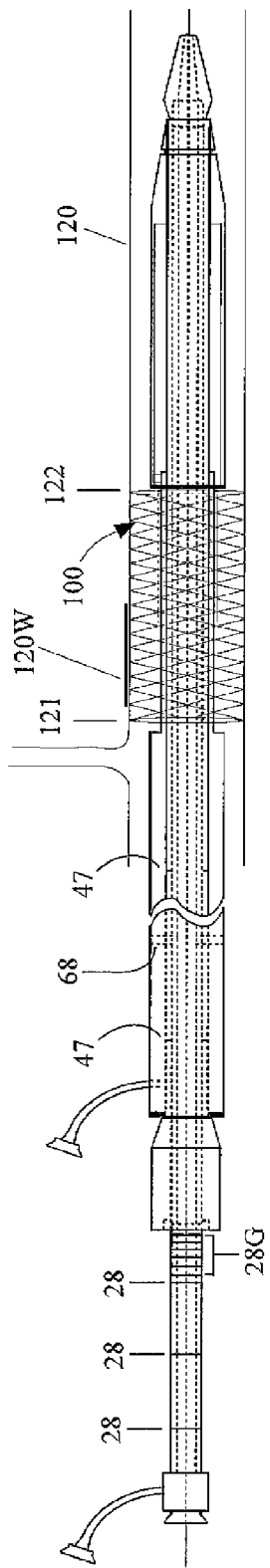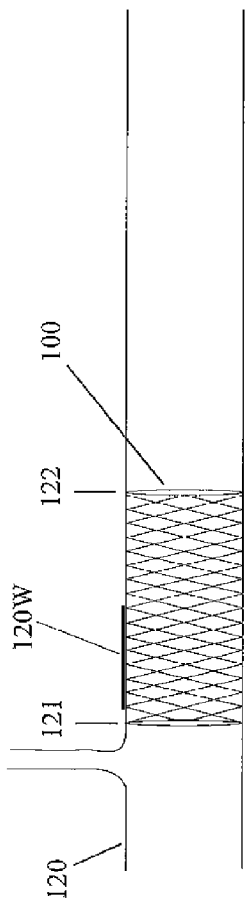

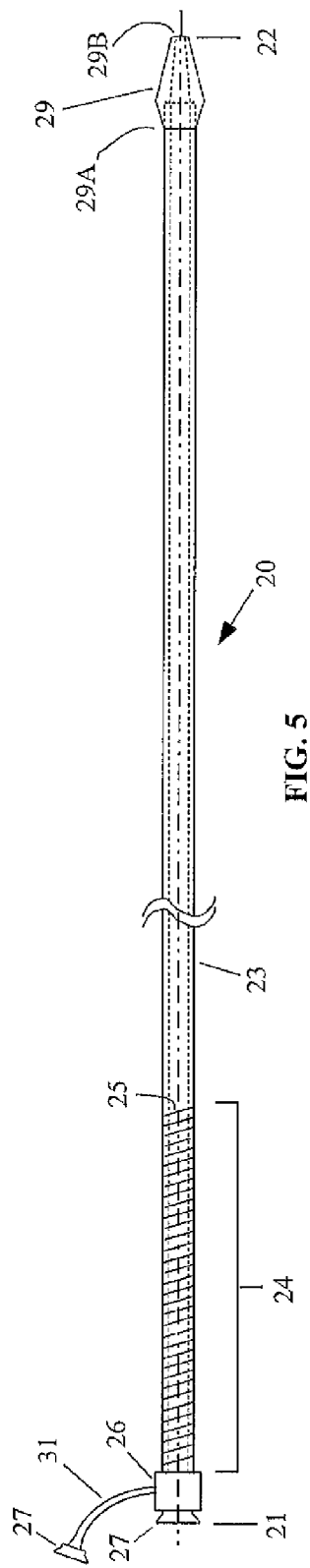
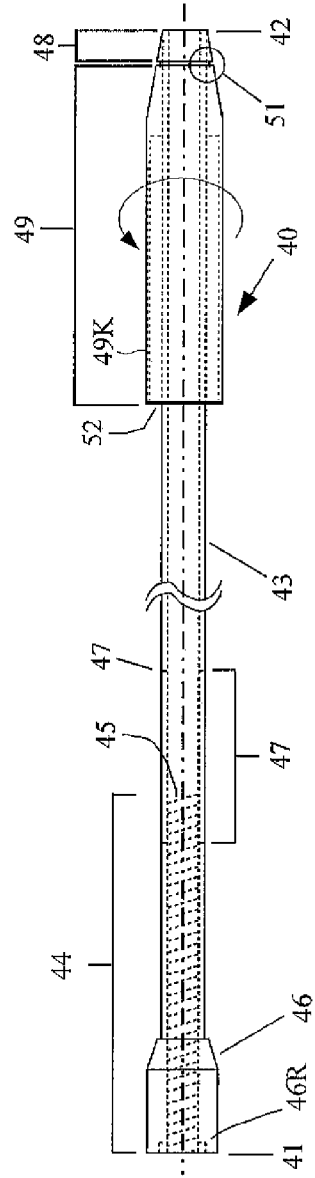
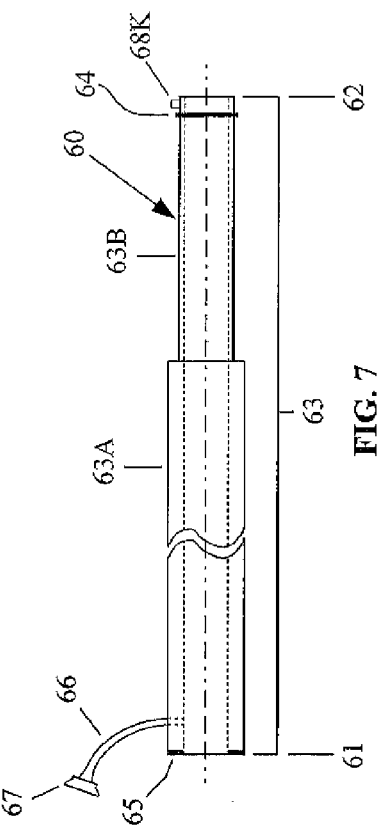
FIG. 5
FIG. 6
FIG. 7

APPARATUS AND METHOD FOR PROXIMAL-TO-DISTAL ENDOLUMINAL STENT DEPLOYMENT

CROSS REFERENCES TO RELATED APPLICATIONS

This application claims priority on U.S. Provisional Application Ser. No. 61/519,238, filed on May 18, 2011, the disclosures of which are incorporated herein by reference.

FIELD OF THE INVENTION

The present invention relates to improvements in methods and apparatus used in the deployment of stents, and more particularly to apparatus which is capable of installing such devices with high fidelity in proximal relation to specific intraluminal locations.

BACKGROUND OF THE INVENTION

The blood vessels and arteries, lymphatic vessels, the ureters of the urinary system, and other ducts within the human body, are subject to degradation. Weaknesses in the walls of these ducts may result from a number of different reasons, such as a ureter being compromised by a kidney stone, or a blood vessel weakening due to atherosclerosis and aging. A minimally invasive surgical treatment for weakened, aneurysmal, or ruptured vessels may comprise the introduction of prosthesis within the lumen. The prosthesis, which often may be a stent, serves to restore some or all of the functionality lost through the deterioration of the vessel and/or bolster the duct's integrity at the site of weakness.

There are many devices that have been developed to introduce a stent into the inner open space or "lumen" of these vessels and ducts. A representative example of these devices is shown by the invention in U.S. Pat. No. 7,867,268 to Shelso, titled, "Stent Delivery System for Self-Expanding Stent." In Shelso, as with virtually most of these devices, a catheter assembly comprises an outer tube, into which a self-expanding stent is loaded, and also comprises a slidable inner tube connected to a tip. The catheter is inserted into the vessel lumen and advanced to the site that is slated to receive the stent. Once properly positioned, the outer tube is backed outward relative to the inner tube with the result that the stent is introduced beginning from the far end- the distal end- and progressively released out from the outer tube to self-expand to contact the vessel wall, until the proximal end of the stent is similarly released and installed. The catheter of the delivery device may then be removed.

A major drawback of all of these devices is that they install the stent in the distal-to-proximal direction. These are several scenarios where the typical distal-to-proximal deployment is highly undesirable, and a means of positioning the stent to have one end at an exact proximal location-requiring a proximal-to-distal deployment-would be extremely advantageous, because placement of the stent at such a proximal location is critical in certain scenarios. Some examples of such scenarios are: where the self-expanding stent is to be deployed in proximity to a location where a side branch originates and the side branch is not to be covered; where a stent is needed to be deployed to overlap another previously installed stent more proximally; and to cover the Ostia of a lumen. The invention herein comprises a new apparatus and corresponding method to achieve a reverse stent deployment installation, to ensure critical proximal stent positioning.

SUMMARY OF THE INVENTION

Throughout this specification, when discussing the blood vessels and other types of ducts, the term distal with respect to the prosthesis refers to the end of the prosthesis furthest away from the position of the medical personnel operating the device. Similarly, the term proximal means the end of the prosthesis, which, when implanted, would be nearest to the medical personnel. Usage of the terms "distal" and "proximal" are also used herein to relatively describe respective ends or portions of different parts/features of the disclosed device, by having the same positional reference with respect to the medical personnel.

A prosthetic delivery device is disclosed herein, being for use in introducing a stent within a lumen through a reverse deployment procedure, with deployment beginning at a proximal end location and finishing at a distal end location. The prosthetic delivery device may comprise an inner tube assembly, a rotation tube assembly, and an outer tube assembly. The rotation tube assembly may be threadably engaged with the inner tube assembly. The outer tube assembly may be received over the rotation tube and be fixed relative to the inner tube. The rotation tube may comprise a sheath that concentrically overlays a portion of the outer tube assembly, beneath which a self-extending stent may be positioned. When the rotation tube is rotated to translate relative to both the inner tube assembly and the outer tube assembly, the stent is exposed and deploys beginning at the proximal location, and ending at the distal location. A guide wire may extend through the inner tube from one end and out of the other end. One or more flush tubes may be used on each of the tube assemblies, where the flush tube terminates in a female syringe adapter that permits threadable attachment of a syringe thereto.

BRIEF DESCRIPTION OF THE DRAWINGS

FIG. 1 is a profile view of the stent delivery apparatus of the current invention, with the delivery sheath shown in the undeployed position to be overhanging a portion of the outer tube, and with a stent stowed therebetween.

FIG. 1A is the profile view of the stent delivery apparatus of FIG. 1, enlarged to show the interface between outer tube and the sheath at the end of the distal end of the stent.

FIG. 1B is the profile view of the stent delivery apparatus of FIG. 1, but shown with the delivery sheath in the fully deployed position, and with a stent prior to being loaded onto the delivery platform of the outer tube, and with a portion of the loaded stent just prior to being crimped.

FIG. 2 is the stent delivery apparatus of FIG. 1, with the delivery sheath being in a partially deployed position and a portion of the stent having self-expanded beginning at the proximal edge of the desired intraluminal location, and with a portion of the stent remaining stowed between the delivery sheath and the outer tube.

FIG. 2A is the stent delivery apparatus of FIG. 2, shown with the sheath fully deployed, with the stent having self-expanded completely to support the vessel wall beginning at the proximal edge of the desired intraluminal location and ending at a distal location, and without the threading on the guide tube to make the graduated markings more visible.

FIG. 3 is a cross-sectional view through the three tubes of the apparatus, being taken at a location where the stent is stowed.

FIG. 4 is the view of FIG. 2A with the stent fully installed, and the stent-delivery apparatus having been removed.

FIG. 5 is a side view of the inner guide tube assembly of the current invention.

FIG. 6 is a side view of the rotation tube assembly of the current invention.

FIG. 7 is a side view of the outer tube assembly of the current invention.

DETAILED DESCRIPTION OF THE INVENTION

FIG. 1 shows a first embodiment of a prosthetic delivery device 10, being particularly adapted for introducing a stent within a lumen of a vessel, through a deployment procedure that is reversed with respect to conventional deployment, where deployment herein begins with the stent self-expanding at a desired proximal end location, and finishing at a distal end location. The main component parts of the prosthetic delivery device 10 comprise an inner guide tube assembly 20, a rotation tube assembly 40, and an outer tube assembly 60, each of which is shown individually within FIGS. 5, 6, and 7 respectfully.

The inner guide tube assembly 20 (FIG. 5) may have a first end 21 and a second end 22. The inner tube assembly 20 may comprise a flexible hollow tube 23 being of sufficient length to reach the sites that are typically the area targeted to receive a stent. A region 24 of the exterior of the inner tube 20, being proximate to the first end 21, may have external threading 25 located thereon. The external threading 25 may be coarse threading, or may be fine threading, as required for a particular type of prosthetic/stent installation being performed. Being secured to the first end 21 of inner tube 20 may be a lock fitting 26, which may extend radially outward from the tube 23, and may comprise a cylindrical shape. The lock fitting 26 may be attached to the tube 20 using any suitable manufacturing means available within the art, including, but not limited to, adhesive bonding, swaging, etc. The lock fitting 26 may also be integrally formed with the tube 20.

The lock fitting 26 may serve multiple functions, which may include limiting the travel of the rotation tube, as discussed hereinafter. In addition, the lock fitting 26 may support a flush tube 31 that may protrude from a portion of the lock fitting. The flush tube 31 may have one end interconnecting with the interior conduit (inner lumen) of tube 23 to be in fluid communication therewith, and may have a female syringe adapter 27 secured at the other end. The syringe adapter 27 may comprise female threading that permits a standard syringe to be screwed thereon to permit flushing of the inner tube 20, to ensure removal of air and/or contaminants therein to prevent them from entering the patient's vasculature. The syringe adapter 27 may be constructed in accordance with U.S. Pat. No. 4,588,403 to Weiss for a "Vented Syringe Adapter Assembly," the disclosures of which are incorporated herein by reference, or it may be constructed per any other suitable syringe adapter known in the art.

The inner lumen of the tube 23 of tube assembly 20 may be appropriately sized so that a guide wire 80 may be slidably received there through. During the prosthetic/stent installation procedure, the guide wire 80 may initially be advanced through the inner lumen of tube 23 to extend out from the second end 22 of the tube, and guide wire 80 may then be maneuvered into the patient's vasculature to a point which is near to, or slightly beyond, the region that is to receive the stent. The guide wire may furthermore function as described within U.S. Pat. No. 4,787,884 to Goldberg for "Ureteral Stent Guidewire System," and within U.S. Pat. No. 6,280,465 to Cryer for "Apparatus and Method for Delivering a Self-Expanding Stent on a Guide Wire," with the disclosures of each being incorporated herein by reference.

The second end 22 of tube 23 of guide tube assembly 20 may comprise a nose cone 29. The nose cone 29 may generally have a diamond-shaped profile, as seen in FIG. 5, the forward facing portion of which may serve to create an aerodynamic tip 29b to reduce friction and resistance while moving the delivery device 10 into and out of a vessel lumen. The nose cone 29 may be attached to the tube 23 using any suitable manufacturing means known in the art, including, but not limited to, adhesive bonding, swaging, etc. The nose cone 29 may alternatively be integrally formed with the tube 23. The nose cone 29 may thus extend radially outward from the tube 23 of inner tube assembly 20. The rear or proximal end 29A of the nose cone 29 may serve to limit travel of the rotation tube 40 at a second position, as discussed hereinafter (see FIG. 1B).

The rotation tube assembly 40 (FIG. 6) may have a first end 41 and a second end 42. The rotation tube assembly 40 may comprise a hollow tube 43, with a region 44 therein having internal threading 45, which may preferably begin at the first end 41, and be selected to threadably engage with the external threading 25 of inner tube 20. The first end 41 of rotation tube assembly 40 may comprise a graspable rotator member 46 being attached thereto, with the graspable rotator extending radially outward from the rotation tube 43. The graspable rotator member 46 may be attached to the tube 23 using any suitable manufacturing means known in the art, including, but not limited to, adhesive bonding, swaging, etc. The graspable rotator member 46 may alternatively be integrally formed with the rotation tube assembly 40. The graspable rotator 46 may serve to provide the tube with a larger diameter feature, which may thereby provide the user of the delivery device with a more ergonomic means of physically grasping the rotation tube 40 to cause its rotation. The end of the graspable rotator 46 coinciding with the first end 41 may have a cylindrical recess 46R therein, which may be of sufficient depth to receive a portion of the cylindrical lock fitting 26.

The second end of the rotation tube 40 may comprise a rotator cone 48 from which a sheath 49 may extend in the proximal direction. The sheath 49 may be connected to the rotator cone using a swivel joint 51, which may permit the rotator cone 48 of the rotation tube 40 to correspondingly rotate with tube 43, without necessitating corresponding rotation of the sheath 49. The swivel joint thus permits relative rotation between the sheath 49 and rotator cone 48. The swivel joint may be constructed similar to the "Swivel Head Cap Connector" of U.S. Pat. No. 5,372,532 to Robertson, or the "Hose Swivel" of U.S. Pat. No. 5,316,351 to Czimny, or the "Swivel Connector" of U.S. Pat. No. 4,955,749 to Panovic, with the disclosures of each being incorporated herein by reference. The sheath may extend from the rotator cone 48 back toward the first end 41, and may be generally concentric with the generally cylindrical tube. 43, but be offset therefrom to create a cylindrical gap into which the stent 100 (FIGS. 1-4) may be inserted. The gap may therefore be calibrated to accommodate, in a clearance fit, the thicknesses of various different stents that may be desirably installed using the device. The stent 100, in order to be self-extending, would be normally biased outward; therefore, the stent 100 may need to be preloaded inwardly to insert it into the cylindrical gap between the sheath 49 and the tube 43 of the rotation tube 40, which is discussed in more detail hereinafter.

The outer tube assembly 60 (FIG. 7) may have a first end 61 and a second end 62. The rotation tube assembly 60 may comprise a tube 63 that may preferably have a first portion comprising an outer cylindrical surface 63A that begins at the first end 61, and which transitions prior to reaching the second end 62, into a second portion having an outer cylindrical surface 63B, which may serve as a stent "platform." Outer surface 63B may have a diameter being slightly smaller than the diameter of outer surface 63A, with this smaller diameter serving to accommodate clearance with the stent 100. Located proximate to second end 62 of the outer tube assembly 60 may be an annular deployment ring 64 protruding radially out from the outer surface 63B, which may serve to precipitate the deployment of the stent 100 out from the annular gap in the sheath 49 of the rotator tube 40. The deployment ring 64 could be a solid protrusion extending radially outward from the outer tube, or may instead be a separated ring secured thereon, from which may protrude a plurality of soft bristles that may be used to gently urge the stent out from the beneath the sheath, without causing damage to the end of the stent during its deployment.

The deployment ring 64, as seen in FIG. 1A, may protrude radially so as to maintain a slight clearance fit with the inner diameter of the sheath 49 of the rotator tube 40. Alternatively, deployment ring 64 may protrude radially so as to engage the inner diameter of the sheath 49 of the rotator tube 40 in a very slight interference fit, to ensure contact with, and deployment of, the stent 100. This interference fit may also serve to deter co-rotation of the swivel-mounted sheath 49, when the rotation tube 40 is being rotated to release the stent 100. Rather than using this interference fit to deter co-rotation of the sheath 49, a key 68K protruding from the second end 62 of outer tube 60 (FIG. 7) may be slidably received within a corresponding keyway 49K on the inside surface of the sheath (FIG. 6) to more positively limit the motion of the swivel-mounted sheath 49 to be only translational motion (FIG. 2), despite the rotational and translation motion that may be experienced by the rotator cone 48.

Located at the first end 61 may be an annular hemostatic seal member 65, which may serve to seal the outer tube 60 with respect to the rotation tube 40. The annular seal member 65 may be made of any suitable sealing material, including, but not limited to, an ethylene propylene elastomer. Located proximate to the first end 61 may be a flush tube 66, which may have one end interconnecting with the interior conduit of tube 63, and may have a female syringe adapter 67 at the other end. The syringe adapter 67 may be similar to female syringe adapter 27, and may comprise female threading that permits a standard syringe to be screwed thereon to permit flushing of the outer tube 60.

The assembled prosthetic delivery device 10 with a self-expanding stent 100 preloaded and inserted therein, is shown in FIG. 1. The outer tube assembly 60 may be slidably received over the rotation tube and be secured to the inner tube assembly 20 using suitable mechanical fasteners 68. The mechanical fasteners 68 may be installed with a sealant material so as to be sealed with respect to the inner tube 23 and with respect to the outer tube 63a. To permit free unrestricted movement of the rotation tube assembly 40, the rotation tube 43 may comprise slotted openings 47 in the region on either side of the fasteners 68.

Rotating the rotation tube assembly 40 may cause it to correspondingly translate relative to both the inner tube assembly 20 and the outer tube assembly 60, so that the recess 46R in the graspable member 46 no longer receives the cylindrical lock fitting 26 at the first position, because the graspable member has translated slightly in the distal direction, as seen in FIG. 1. The sheath 49 similarly translates, and with continued rotating of the rotation tube assembly 40, the nose cone 48 of the rotation tube assembly may eventually contact the proximal end 29a of the diamond-shaped nose cone 29 at the second end 22 of tube 23 of guide tube assembly 20, to thereby limit travel of the rotation tube 40 at a second position, as seen in FIG. 1B.

With the rotation tube 40 being rotated to occupy this second position, the stent 100 may be loaded thereon in order to prepare a fully assembled prosthetic delivery device 10 that is ready to perform the prosthetic installation. The free-standing, self-expanded stent $100_E$ in FIG. 1B is first loaded across the nose cone 29, the nose cone 49, and the sheath 49, and onto the "platform" of outer surface 63B, after which it may be preloaded inward for insertion beneath the sheath 49 of the rotation tube 40. Insertion of the stent 100 beneath the sheath 49 may be done by manually crimping and causing a size reduction of the expandable stent, as had been done in the past, or by using a specially constructed device, such as the one shown by U.S. Pat. No. 7,992,273 to Austin for "Crimping Apparatus for Reducing Size of a Stent," as well as by a device disclosed by one of the references cited therein, with the disclosures of each being incorporated herein by reference. As crimping of the stent $100_C$ occurs, which is initially adjacent to the deployment ring 64, the sheath 49 may be backed to overhang more of cylindrical surface 63B and overhang the crimped portion of the stent, as the sheath moves back toward the first cylindrical surface 63A, by counter-rotating the rotation tube assembly 40.

FIG. 2 shows the fully assembled prosthetic delivery device 10 having been advanced within a lumen 120 of a patient to the site requiring proximal-to-distal stent deployment, and with the self-expanding stent 100 initially expanding precisely at the desired proximal location 121, being near a weakened region 120W. Continued rotation of the rotation tube 40 may continue until the stent 100 is fully deployed at the distal end 122 within body lumen 120, as seen in FIG. 2A. The device 10 may then be removed from the lumen, which had then been reinforced by the stent 100, as seen within FIG. 4.

To assist the practitioner who is performing the stent deployment procedure, the inner tube 23 may contain graduated markings 28 that may be exposed, as the rotation tube assembly translates distally, in order to inform the practitioner as to the progress made in deploying the stent. In addition, the graduated markings 28 may transition into a series of graduated markings 28G having a smaller spacing therebetween, to inform the practitioner as to when the sheath should be translated sufficiently so that the stent has been fully deployed, and also as to when the second end of the rotation tube is nearing contact with the rear portion of the nose cone 29. Alternatively, or in addition to such markings 28, completed travel of the rotation tube, at which time the stent should be fully deployed, may occur and be indicated by the second end 42 of the rotation tube contacting a rear portion of, or the proximal end 29a of, the nose cone 29.

The examples and descriptions provided merely illustrate a preferred embodiment of the present invention. Those skilled in the art and having the benefit of the present disclosure will appreciate that further embodiments may be implemented with various changes within the scope of the present invention. Other modifications, substitutions, omissions and changes may be made in the design, size, materials used or proportions, operating conditions, assembly sequence, or arrangement or positioning of elements and members of the preferred embodiment without departing from the spirit of this invention.

I claim:

1. A stent placement device, for use in placing a stent within a patient's vasculature through a reverse deployment procedure, with deployment beginning at a proximal location and ending at a distal location, said prosthetic delivery device comprising:

a guide tube having a proximal end and a distal end; a portion of said guide tube comprising external threading;

a rotation tube having a proximal end and a distal end, a portion of an inner surface of said rotation tube comprising internal threading configured to threadably engage with said external threading of said guide tube;

a sheath, said sheath attached in proximity to said distal end of said rotation tube, and configured to extend toward said proximal end of said rotation tube;

an outer tube having a proximal end and a distal end, an inner surface of said outer tube configured to receive a portion of said rotation tube therein;

wherein when said rotation tube is at a first position relative to said guide tube, said sheath is configured to overhang a portion of an outer surface of said outer tube, said portion of said outer surface of said outer tube being from proximate to its distal end to a position between its distal and proximal ends; said portion of said outer surface of said outer tube configured to provide a clearance gap with an inner surface of said sheath, to receive an outwardly biased self-expanding stent therein;

means of fixedly securing said outer tube to said guide tube, while permitting relative motion of said rotation tube thereto;

a deployment ring configured to protrude outwardly from said outer surface of said outer tube;

wherein rotation of said rotation tube relative to said guide tube causes said threaded engagement therebetween to cause corresponding movement of said rotation tube, distally, from said first position to a second position; and wherein said distal movement of said rotation tube is configured to correspondingly cause movement of said sheath relative to said deployment ring, with said deployment ring configured to urge deployment of the stent out from said gap, to permit said proximal-to-distal stent deployment.

2. The stent placement device according to claim 1 wherein said sheath being attached proximate to said distal end of said rotation tube comprises a swivel connection therebetween, said swivel connection configured to permit said rotation of said rotation tube without necessitating corresponding rotation of said sheath.

3. The stent placement device according to claim 2 wherein said outwardly protruding deployment ring is configured to protrude into contact with said inner surface of said sheath, said contact configured to inhibit rotation of said sheath relative to said outer tube during said distal movement of said rotation tube for said proximal-to-distal stent deployment.

4. The stent placement device according to claim 3 wherein said deployment ring comprises a plurality of soft bristles configured to extend radially therefrom.

5. The stent placement device according to claim 4 wherein said distal end of said guide tube comprises a nose cone fixedly secured thereto, said nose cone having a proximal end configured to limit said distal movement of said rotation tube to said second position by contact of a distal end of said rotation tube with said proximal end of said nose cone; said second position comprising a position whereat said distal movement of said rotation tube has caused a proximal end of said sheath to reach said deployment ring.

6. The stent placement device according to claim 5 wherein said proximal end of said guide tube comprises a lock fitting fixedly secured thereto, and said proximal end of said rotation tube comprises a graspable rotator fixedly secured thereto; and wherein said lock fitting is configured to limit distal-to-proximal travel of said rotation tube to said first position.

7. The stent placement device according to claim 6 wherein said guide tube comprises a plurality of graduated markings, each of said plurality of graduated marking configured to indicate progress of said rotation tube in said distal movement from said first position toward said second position.

8. The stent placement device according to claim 7 further comprising a plurality of incrementally smaller-spaced markings configured to indicate when said distal movement of said rotation tube has caused said rotation tube to nearly reach said second position.

9. The stent placement device according to claim 8 further comprising a flush tube and a syringe adapter, said flush tube fixedly secured to said lock fitting and having a first end therein configured to interconnect with an interior of said guide tube; and wherein a second end of said flush tube is coupled to said syringe adapter.

10. The stent placement device according to claim 9 further comprising a second flush tube and a second syringe adapter, said second flush tube fixedly secured to said outer tube and configured to interconnect with an interior of said outer tube; and wherein a second end of said second flush tube is coupled to said second syringe adapter.

11. The stent placement device according to claim 10 wherein said outer surface of said outer tube comprises:

a first outer surface portion having a first diameter and beginning at said proximal end of said outer tube; and a second outer surface portion having a second diameter and beginning at said distal end of said outer tube, with said first outer surface portion configured to transition to said second outer surface portion between said proximal and distal ends of said outer tube, said second diameter being smaller than said first diameter.

12. The stent placement device according to claim 11 wherein said guide tube comprises an inner lumen configured to slidably receive a guide wire therein.

13. The stent placement device according to claim 2 wherein said outer tube comprises a key, and said inner surface of said sheath comprises a keyway, said key being slidably received in said keyway to inhibit rotation of said sheath relative to said outer tube, during said distal movement of said rotation tube for said proximal-to-distal stent deployment.

14. The stent placement device according to claim 13 wherein said deployment ring comprises a plurality of soft bristles configured to extend radially therefrom deployment ring.

15. The stent placement device according to claim 14 wherein said distal end of said guide tube comprises a nose cone fixedly secured thereto, said nose cone having a proximal end configured to limit said distal movement of said rotation tube to said second position; said second position comprising a position whereat said distal movement of said rotation tube has caused a proximal end of said sheath to reach said deployment ring.

* * * * *